(12) United States Patent
Shafirstein et al.

(10) Patent No.: US 9,687,268 B2
(45) Date of Patent: Jun. 27, 2017

(54) DERMATOME WITH ADJUSTABLE WIDTH AND DEPTH GUARDS

(71) Applicants: Gal Shafirstein, Amherst, NY (US); Anjay K. Khandelwal, Cleveland, OH (US); James C. Walker, Little Rock, AR (US)

(72) Inventors: Gal Shafirstein, Amherst, NY (US); Anjay K. Khandelwal, Cleveland, OH (US); James C. Walker, Little Rock, AR (US)

(73) Assignees: BioVentures, LLC, Little Rock, AR (US); Arkansas Children's Research Institute, Little Rock, AR (US)

( * ) Notice: Subject to any disclaimer, the term of this patent is extended or adjusted under 35 U.S.C. 154(b) by 114 days.

(21) Appl. No.: 14/183,788

(22) Filed: Feb. 19, 2014

(65) Prior Publication Data
US 2014/0236180 A1    Aug. 21, 2014

Related U.S. Application Data

(60) Provisional application No. 61/766,513, filed on Feb. 19, 2013.

(51) Int. Cl.
*A61B 17/50*    (2006.01)
*A61B 17/322*    (2006.01)

(52) U.S. Cl.
CPC .................. *A61B 17/322* (2013.01)

(58) Field of Classification Search
CPC ........................................ A61B 17/322
USPC ............................................ 606/132
See application file for complete search history.

(56) References Cited

U.S. PATENT DOCUMENTS

| | | | | |
|---|---|---|---|---|
| 2,457,772 | A * | 12/1948 | Brown et al. | A61B 17/322 606/132 |
| 3,670,734 | A * | 6/1972 | Hardy, Jr. | A61B 17/322 606/132 |
| 3,820,543 | A * | 6/1974 | Vanjushin et al. | A61B 17/322 30/394 |
| 2005/0234485 | A1* | 10/2005 | Seegert | A61B 17/322 606/172 |
| 2005/0240124 | A1* | 10/2005 | Mast | A61N 7/022 601/2 |
| 2009/0138027 | A1 | 5/2009 | Lucas | |
| 2009/0157096 | A1 | 6/2009 | Boles | |
| 2009/0240261 | A1* | 9/2009 | Drews | A61B 10/0266 606/133 |

* cited by examiner

*Primary Examiner* — Kristen Matter
(74) *Attorney, Agent, or Firm* — Richard Blakely Glasgow

(57) ABSTRACT

A dermatome including a battery unit, a handle, and a head portion. The head portion includes guards capable of being adjusted to control the width and the depth of the cut without an interruption in the medical procedure.

17 Claims, 8 Drawing Sheets

DERMATOME WITH ADJUSTABLE WIDTH AND DEPTH GUARDS

CROSS-REFERENCE TO RELATED APPLICATIONS

This application claims the benefit of U.S. Provisional Application No. 61/766,513, entitled "Dermatome with Adjustable Width and Depth Guards" and filed on Feb. 19, 2013. The complete disclosure of said provisional patent application is hereby incorporated by reference.

STATEMENT REGARDING FEDERALLY FUNDED SPONSORED RESEARCH OR DEVELOPMENT

Not applicable

BACKGROUND OF THE INVENTION

1. Field of the Invention

The present invention relates generally to a device for harvesting skin and excising burns, and in particular to a dermatome with adjustable guards to control the width and depth of the cut without interruption of the medical procedure.

2. Brief Description of the Related Art

A dermatome is a medical instrument that has used since the 1940's when it was developed for a split thickness skin graft. A skin graft is a patch of healthy skin that is harvested from one area of the body or donor site to cover a damaged or skinless area of the body. Surgeons recently have been using a dermatome for excising burn wounds, especially over relatively flat surfaces such as the back, chest, and lower extremities.

Depending on the area of the body, the extent of the damaged tissue, and other factors, the width and depth of the skin being harvested or burned tissue being excised will vary. To allow for this variance, the prior art dermatomes comprise attachable guards that control the portion of the blade that is exposed to the skin. The greater the portion of the blade exposed laterally, the greater the width of the cut. The greater the height of blade exposed from the front edge of the device, the greater the depth of the cut. To adjust the width of the cut during the medical procedure, however, the guard has to be mechanically changed. This changing process consists of stopping the medical procedure, disconnecting the dermatome, detaching the guard (e.g. unscrewing the guard from the dermatome), attaching the new guard (e.g. screwing the guard to the dermatome), and resuming the medical procedure. This process is very time consuming, which wastes valuable operating room time.

In addition, prior art dermatomes are not designed for both harvesting skin and excising burned tissue. Thus, in order to excise burns, several runs at the maximum blade depth of the dermatome is often required. This process can also be very time consuming and thus costly to the patient.

Many of the prior art dermatomes are air-powered, thus relying on an air connection, which requires a long, heavy tubing that interferes with the surgeon and can clutter the operative field. Because of the pressure exerted on the dermatome, the prior art dermatomes are generally made of steel or other strong materials. As a result, the dermatomes are heavy and often difficult to maneuver. It has also been observed that the blade of the prior art dermatomes often becomes dull very quickly. On average, after four harvests of skin, or two excisions of burns, the blade must be changed. The blade changing process involves disconnecting the dermatome, detaching the guard, changing the blade, reattaching the guard, and then reconnecting the dermatome.

Moreover, prior art dermatomes designed to excise burned tissue utilize blades that have been in practice for over 60 years. The blades are known for frequently digging into the skin during excision creating lacerations that must be repaired. In addition, they produce ragged edges that can be cosmetically unsightly.

It would therefore be desirable to develop a dermatome with adjustable guards to control both the width and the depth of the cut without interruption of the skin harvesting or burn excision procedure.

It would also be desirable to develop a dermatome that is capable of excising damaged tissue with a single pass.

It would also be desirable to develop a dermatome that is lighter in weight, battery-powered, and has a blade that will allow multiple harvests and excisions without necessitating a blade change.

BRIEF SUMMARY OF THE INVENTION

The present invention is directed to a dermatome comprising a battery, a handle, and a head portion, wherein said head portion comprises guards capable of being adjusted to control the width and the depth of the cut without an interruption in the medical procedure.

These and other features, objects and advantages of the present invention will become better understood from consideration of the following detailed description of the preferred embodiments, in conjunction with the drawings as described immediately below.

DETAILED DESCRIPTION OF THE INVENTION

Figure 1A:
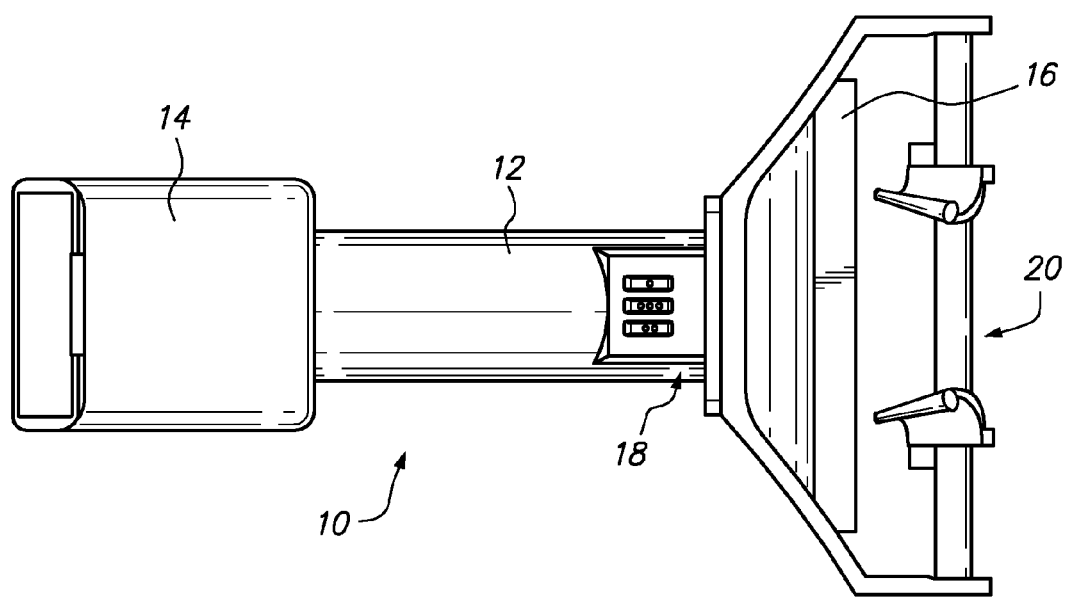
FIG. 1A is a top plan view of the dermatome of the present invention.
Figure 1B:
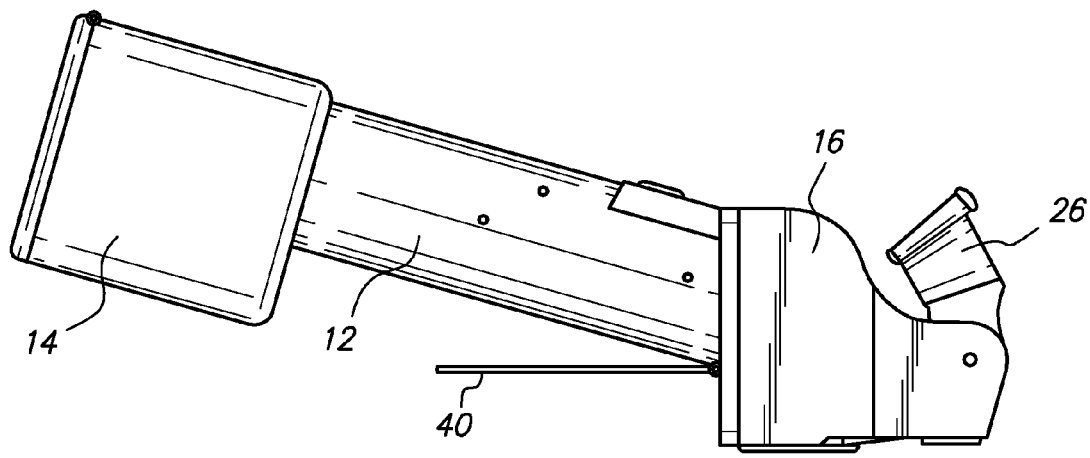
FIG. 1B is a right side elevational view of the dermatome of the present invention.

With reference to FIGS. 1-11, the preferred embodiments of the present invention may be described. The dermatome 10 is comprised of a handle 12, a battery unit 14, and a head unit 16. The handle 12 is attached to the battery unit 14 at one end and the head unit 16 at the other end. As shown in FIG. 1A from a top view, the head unit 16 is substantially an irregular hexagon shape. The back end 18 of the head unit 16, which is the end attached to the handle 12, is parallel to the front end 20 of the head unit 16, which is at the opposite end of the head unit 16. The back end 18 of the head unit 20 is shorter in length than the front end 20 of the head unit 16. As shown in FIG. 1B, the head unit 16 slopes from the back end 18 of the head unit 16 to the front end 20 of the head unit 16.

Figure 2:
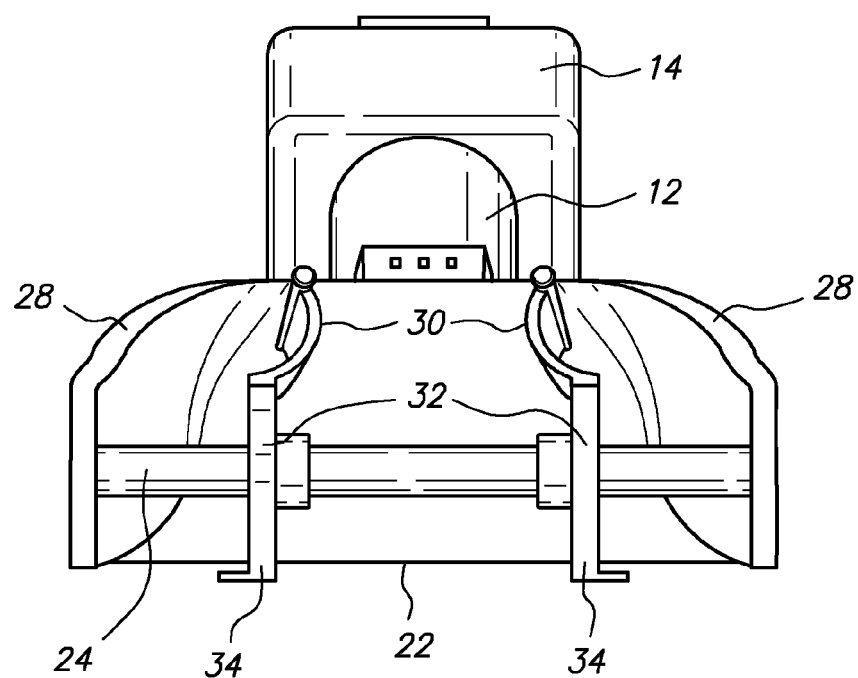
FIG. 2 is a front elevational view of the dermatome of the present invention.
Figure 11:
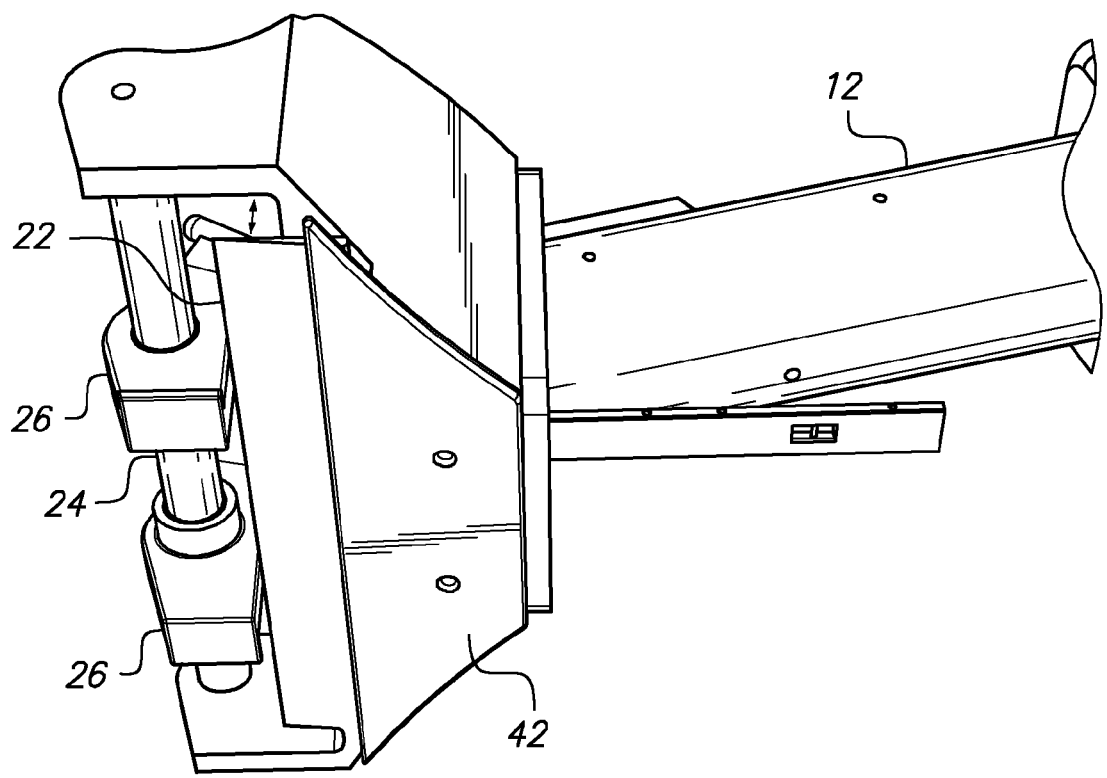
FIG. 11 is a bottom left perspective view of the head unit of the dermatome of the present invention.

As shown in FIG. 2 and FIG. 11, the front end 20 of head unit 16 comprises a blade 22, an axle 24, and two blade guard units 26. The axle 24 extends across the length of the front end 20 of the head unit 16, thus between the left side wall 28 and right side wall 28 of the head unit 16. The axle 24 is preferably cylindrical in shape. Two blade guard units 26 are received by the axle 24. Each blade guard unit 26 is comprised of a top section 30, middle section 32, and bottom section 34. The middle section 32 is substantially vertical and comprises a circular hole in the middle where the blade guard unit 26 is received by the axle 24. Attached to the middle section 32 at one end is top section 30, which is arc-shaped. Attached to the middle section 32 at the opposite end is bottom section 34. The bottom section 34 extends perpendicularly to the middle section 32. The bottom sections 34 of the two blade guard units 26 extend away from each other towards the left and right ends 28 of the head unit 16. The blade 22 abuts the bottom sections 34 of the blade guard units 26. Thus, the blade edge is only exposed on the portion of the blade between the two blade guard units 26. Because bottom sections 34 of the blade guard units 26 may contact the skin of the patient when the distance between the blade guard units 26 is maximized for wide cuts, in an alternative embodiment, bottom sections 34 of blade guard units 26 may be curved at their ends to avoid contact with the skin.

Figure 8:
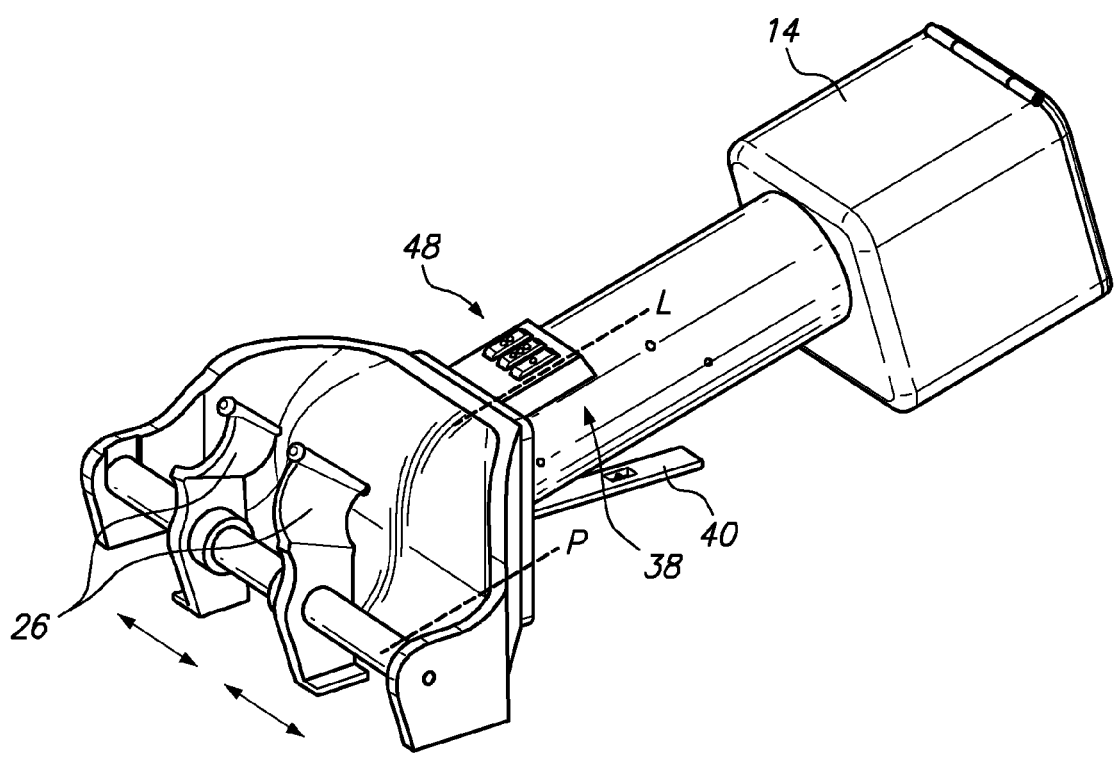
FIG. 8 is a left top perspective view of the dermatome of the present invention.

As shown in FIG. 8, the arc-shaped top section 30 allows the medical professional operating the dermatome 10 to easily grab the blade guard unit 26 and move it left or right along the axle 24. In this regard, the width of the cut can be controlled in real time. For example, as the physician is moving the dermatome across the surface of the patient's skin, the physician can manually move the blade guard units to increase or decrease the width of the cut of skin or skin tissue being removed from the patient. In addition to moving side-to-side along the axle 24, in one embodiment, the blade guard units may be rotated on the axle 24 from the front end 20 of the head unit 16 to the back end 18, and vice versa. While the blade guard units 26 can be manually moved along the axle 24, in an alternative embodiment, the blade guard units 26 can be moved relative to one another by electronic means.

As shown in FIG. 11, blade 22 is secured between a blade plate 42 and the bottom surface of head unit 16. The blade plate 42 and the bottom surface of the head unit 16 are preferably attached via two screws. In the preferred embodiments, however, the blade 22 is not permanently attached to either the head unit 16 or the blade plate 42. The blade 22 has a sharp blade edge facing outward from the front end 20 of the head unit 16 of the dermatome 10, which generally defines a plane P that is generally parallel to longitudinal axis L as shown in FIG. 8. The axis L is generally defined by the dermatome 10 such that the handle 12 also generally extends along axis L.

Figure 7:
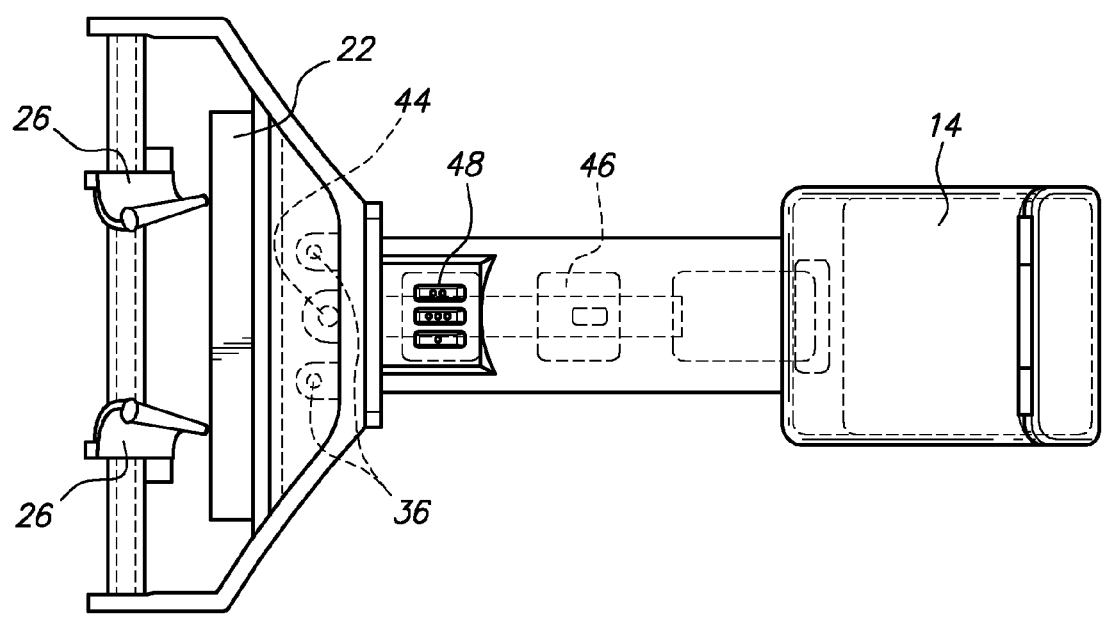
FIG. 7 is a top plan cut-away view of the dermatome of the present invention with internal features shown by broken lines.

As shown in FIG. 7, a blade driver 44 is in communication with the blade 22, which allows the blade 22 to oscillate and cut the skin tissue when the sharp blade edge makes contact with the skin tissue. The blade driver is preferably a rotational motor and is of the type well-known to those skilled in the art. The blade 22 can preferably move laterally approximately five millimeters.

The dermatome 10 also comprises a depth adjuster system. The depth adjuster allows the surgeon to adjust the depth of the blade 22 that is exposed to the patient's skin and thus control the depth of the skin harvested or tissue excised during the surgery. As shown in FIG. 7, the depth adjuster system is comprised of two stepper motor actuators 36 in communication with means for activating the actuators, preferably a button panel 48. Two actuators are preferable for safety and stability of the dermatome 10. By pushing button 50, the actuator 36 extends the blade 22 in increments (e.g. $2/1000$ inch) towards the front end 20 of the head unit 16. By protracting the blade, the portion of the blade 22 that is exposed is increased. In one embodiment, in addition to moving the blade forward, the blade is also tilted downwardly. Button 50 can subsequently be pushed to further adjust the blade exposure as necessary for the particular medical procedure. In contrast, by pushing button 52, the blade 22 is retracted away from the front end 20 of the head unit 16 and the exposed blade is decreased by an increment, such as $2/1000$ inch. Button 52 can also be pushed again to adjust the blade exposure as necessary for the particular medical procedure. In an alternative embodiment, the blade 22 can be controlled by buttons 50, 52 allowing the user of the dermatome to also change the blade angle on the fly (i.e. in real time). The depth adjuster system and blade 22 are configured to cut as small as $30/1,000$ inch of skin tissue.

In an alternative embodiment, the depth adjuster system can be controlled electronically through use of one or more lasers and one or more sensors in the dermatome 10. As the dermatome 10 contacts the skin of the patient, the laser (not shown) emits light through the skin. The reflected light is then received by a sensor (not shown). The amount of light received by the sensor will differ depending on the depth of the damaged tissue. The laser and sensor are integrated into a feedback system in which the blade guard units 26 and depth adjuster system can be electronically altered to ensure that only damaged tissue is cut. As an alternative to a laser, a low powered ultrasound (not shown) could also be used in this feedback system.

The blade 22 comprises a low friction coating, preferably Teflon® coating or carbon-like diamond coating which allows multiple harvests and/or excisions without the need to lubricate or change the blade. The battery 14 alleviates the need for heavy tubing and an air connection, thus making the dermatome 10 lighter and easier to operate. The dermatome is preferably made of aluminum, magnesium alloys, or other composite materials. These materials are significantly lighter than steel.

Figure 3:
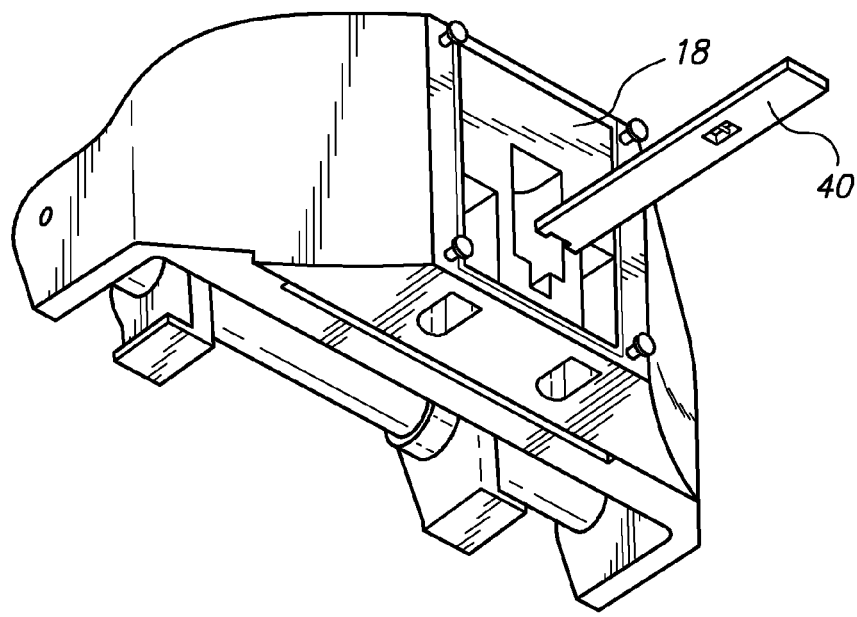
FIG. 3 is a bottom left perspective view of the head unit of the dermatome of the present invention.
Figure 4:
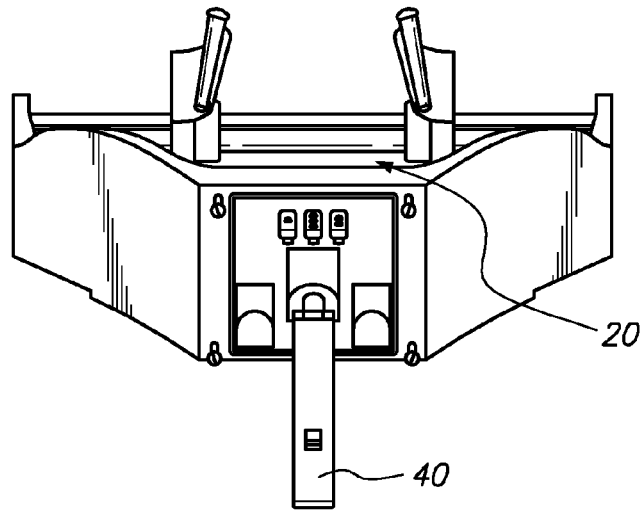
FIG. 4 is a top rear perspective view of the head unit of the dermatome of the present invention.
Figure 5:
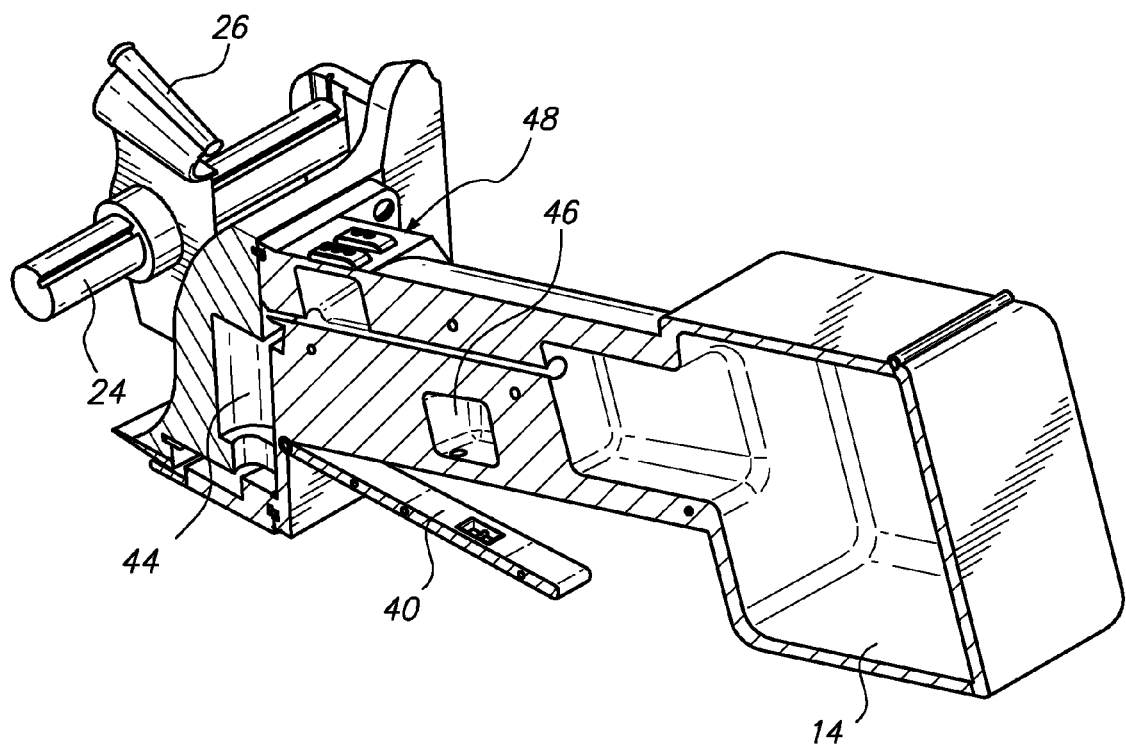
FIG. 5 is a sectional perspective view from the top left of the dermatome of the present invention.
Figure 6:
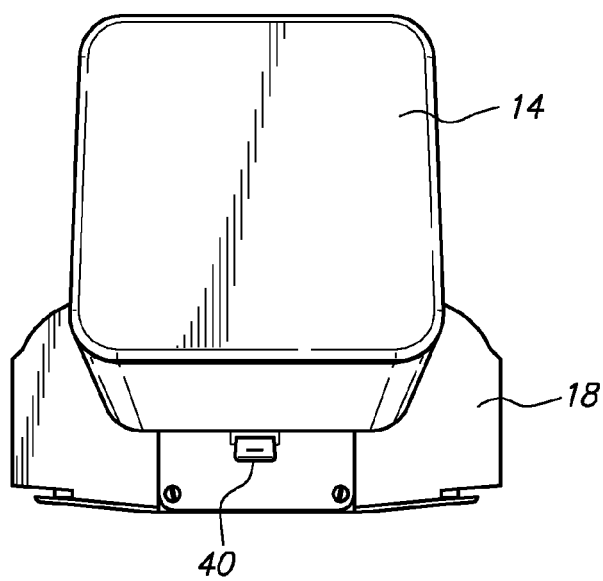
FIG. 6 is a back view of the dermatome of the present invention.
Figure 9:
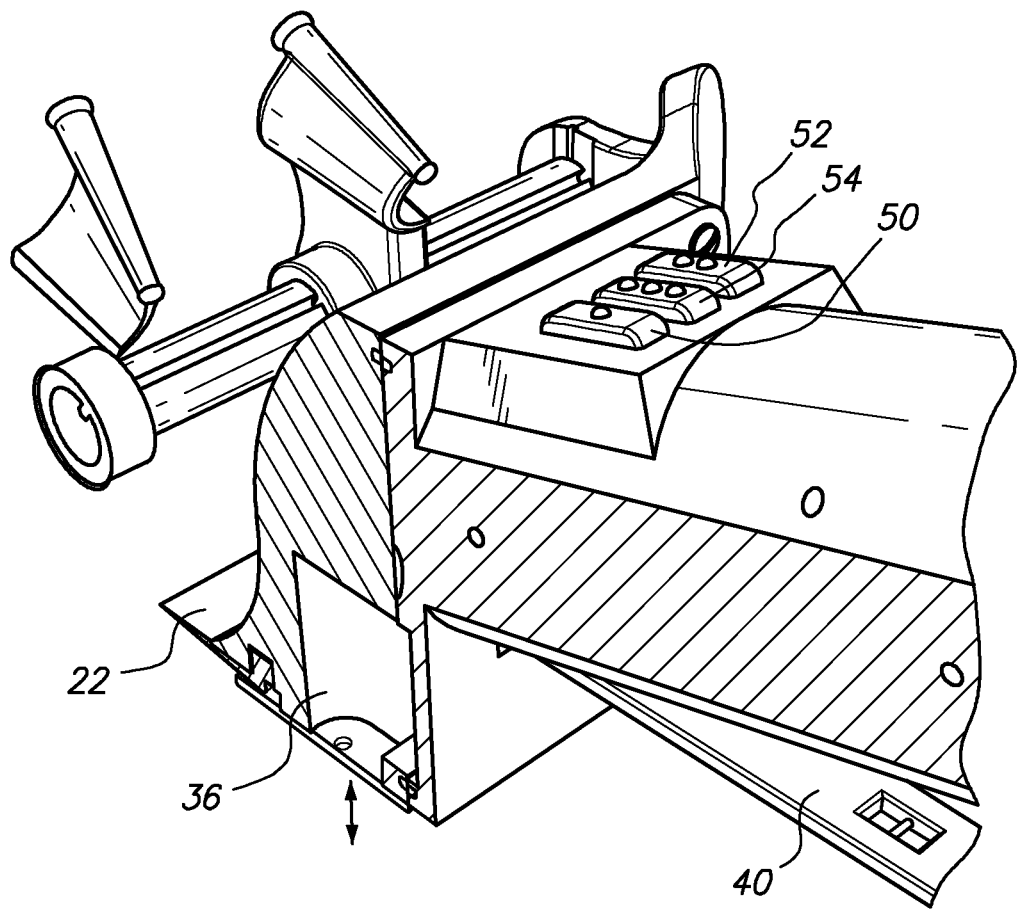
FIG. 9 is a perspective sectional view from the top left of the dermatome of the present invention.
Figure 10:
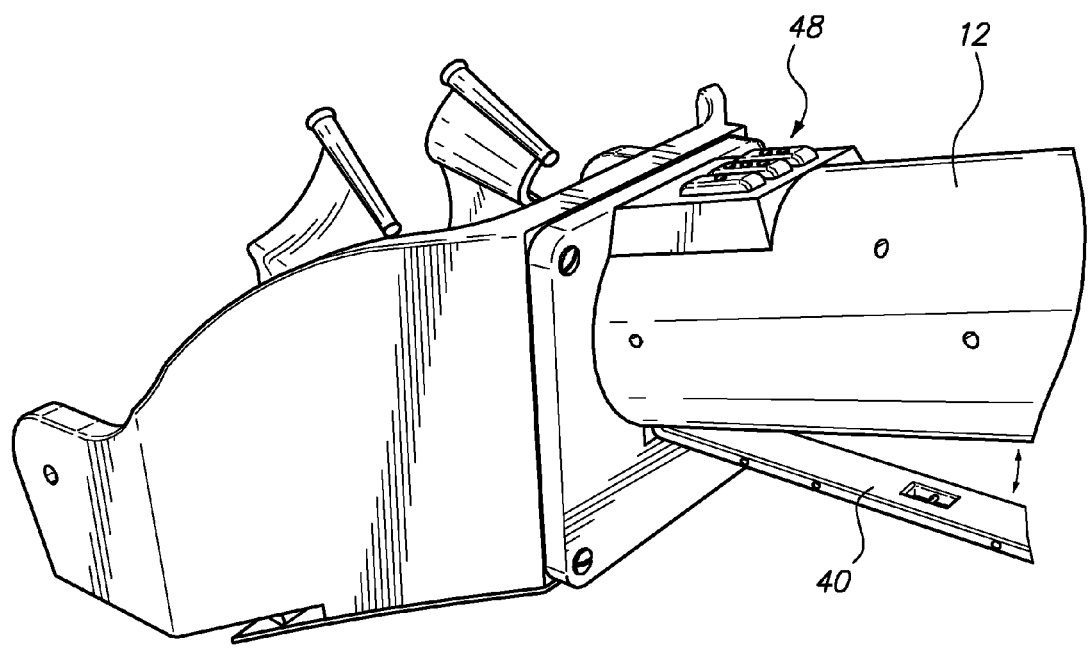
FIG. 10 is a perspective view from the top left of the dermatome of the present invention.

As shown in FIGS. 3-4, the head unit 16 and the handle 12 are attached via complementary connectors found on the back end 18 of head unit 16 and the front end 38 of the handle 12. By holding the lever 40 on the back end 20 of the head unit 16, power is supplied from the battery 14 to allow movement of the blade 22. The lever 40 is in communication with the other portions of the dermatome 10 via a circuit board or processor of the type that is well-known to those skilled in the art. In one embodiment, the dermatome 10 is also comprised of a safety button 54 located on the button panel 48. In this embodiment, the lever 40 must be held and the safety button 54 pushed before power is supplied from the battery 14. To stop the motion of the blade 22, the lever 40 can be released. FIGS. 5, 7 and 9 show the inner mechanical workings of the power system of the dermatome 10, including the battery 14 and the power switch 46, which is in communication with the lever 40. The battery 14 is preferably a standard non-sterile ortho pack which is well-known to those skilled in the art.

The present invention has been described with reference to certain preferred and alternative embodiments that are intended to be exemplary only and not limiting to the full scope of the present invention.

What is claimed is:

1. A device for harvesting skin, comprising a handle, a battery unit, and a head unit, wherein said head unit comprises:
    (a) an axle having a first half and a second half, wherein said axle is connected between a right side wall of said head unit and a left side wall of said head unit;
    (b) a blade having a blade edge; and
    (c) two blade guard units slidably receiving said axle, wherein each of said two blade guard units is laterally adjustable on said first half and said second half of said axle in real time, wherein said device further comprises a depth adjuster system comprising two stepper motor actuators, wherein said two stepper motor actuators are activatable via a button panel comprising a first button and a second button, wherein said blade is retractable by pushing said first button.

2. The device of claim 1, wherein each of said two blade guard units comprises a top portion, a middle portion, and a bottom portion.

3. The device of claim 2, wherein said top portion is arc-shaped.

4. The device of claim 3, wherein said top portion is operable for gripping.

5. The device of claim 2, wherein said middle portion extends vertically between said top portion and said bottom portion.

6. The device of claim 2, wherein said bottom portion prevents a portion of said blade edge of said blade from being exposed at a front end of said head unit.

7. The device of claim 1, wherein said blade is secured to a blade plate.

8. The device of claim 7, wherein said blade plate is connected to a bottom of said head unit.

9. The device of claim 1, further comprising a blade driver in communication with said blade for oscillating said blade.

10. The device of claim 1, wherein said blade is protractable by pushing said second button.

11. The device of claim 1, wherein said blade comprises a low friction coating.

12. The device of claim 1, wherein said blade is adapted to cut $30/1,000$ inch of a skin tissue.

13. The device of claim 1, wherein said head unit and said handle are attached via complementary connectors.

14. The device of claim 1, wherein said head unit comprises a lever for controlling power to said blade.

15. A method for harvesting skin, wherein said method comprises:
    (a) positioning a device for harvesting skin on a skin surface of a subject, wherein said device for harvesting skin comprises a handle, a battery unit, and a head unit, wherein said head unit comprises:
    an axle having a first half and a second half, wherein said axle is connected between a right side wall of said head unit and a left side wall of said head unit;
    a blade having a blade edge; and
    two blade guard units slidably receiving said axle, wherein each of said two blade guard units is laterally adjustable on said first half and said second half of said axle;
    (b) moving said device for harvesting skin across said skin surface of said subject, wherein said blade edge cuts a first width of a skin from said skin surface of said subject, wherein said first width of said skin corresponds to a first distance between said two blade guard units;
    (c) laterally adjusting said two blade guard units on said first half of said axle in real time, wherein said first distance between said two blade guard units is increased or decreased to yield a second distance; and
    (d) moving said device for harvesting skin across said skin surface of said subject, wherein said blade edge cuts a second width of said skin from said skin surface of said subject, wherein said second width of said skin corresponds to said second distance between said two blade guard units.

16. A device for harvesting skin, comprising a handle, a battery unit, and a head unit, wherein said head unit comprises:
    (a) an axle positioned between a first side wall and a second side wall;
    (b) a blade; and
    (c) two blade guard units attached to said axle, wherein said two blade guard units are laterally adjustable on said axle in real time, wherein each of said two blade guard units comprises a top portion, a middle portion, and a bottom portion, wherein said top portion is joined to said middle portion and said middle portion is joined to said bottom portion, wherein said top portion of each of said two blade guard units is arc-shaped and faces said first side wall or said second side wall.

17. The device of claim 16, wherein said top portions of said two blade guard units face in opposite directions.

* * * * *